United States Patent
Pasternak et al.

(10) Patent No.: US 9,892,557 B2
(45) Date of Patent: Feb. 13, 2018

(54) INTEGRATED SYSTEM FOR FOCUSED TREATMENT AND METHODS THEREOF

(71) Applicant: UC-CARE LTD., Yokneam (IL)

(72) Inventors: Alex Pasternak, Tel Aviv (IL); Roni Zvuloni, Haifa (IL); Tomer Schatzberger, Tel Aviv (IL); Shaike Schatzberger, Haifa (IL); Keren Shapira-Schweizer, Tal El (IL); Moshe Ebenstein, Haifa (IL); Michael Cohen, Haifa (IL)

(73) Assignee: UC-CARE LTD., Yokneam (IL)

( * ) Notice: Subject to any disclaimer, the term of this patent is extended or adjusted under 35 U.S.C. 154(b) by 667 days.

(21) Appl. No.: 14/374,910

(22) PCT Filed: Jan. 24, 2013

(86) PCT No.: PCT/IL2013/050065
§ 371 (c)(1),
(2) Date: Jul. 27, 2014

(87) PCT Pub. No.: WO2013/111133
PCT Pub. Date: Aug. 1, 2013

(65) Prior Publication Data
US 2015/0045648 A1 Feb. 12, 2015

Related U.S. Application Data

(60) Provisional application No. 61/590,932, filed on Jan. 26, 2012, provisional application No. 61/655,024, filed on Jun. 4, 2012.

(51) Int. Cl.
*G06T 19/00* (2011.01)
*A61B 10/02* (2006.01)
(Continued)

(52) U.S. Cl.
CPC .......... *G06T 19/003* (2013.01); *A61B 5/0013* (2013.01); *A61B 5/0035* (2013.01);
(Continued)

(58) Field of Classification Search
CPC ......... A61B 8/12; A61B 8/0841; A61B 8/085; A61B 8/4254; A61B 10/0241;
(Continued)

(56) References Cited

U.S. PATENT DOCUMENTS 6,019,725 A 2/2000 Vesely
7,179,219 B2 2/2007 Matlock
(Continued)

FOREIGN PATENT DOCUMENTS

EP 0459535 12/1991
EP 1335270 8/2003
(Continued)

OTHER PUBLICATIONS

Lindseth, Ultrasound Guided Surgery: Multimodal Visualization and Navigation Accuracy, Norwegian University of Science and Technology, Dec. 2002.*
(Continued)

*Primary Examiner* — Bo J Peng
(74) *Attorney, Agent, or Firm* — Dorsey & Whitney LLP

(57) ABSTRACT

An integrated system for facilitating local treatment in an organ and capable of universally interfacing with other devices and systems is provided. The integrated system comprises an imaging system interface module configured to functionally associate with an imaging system capable of presenting to a user, through a user-interface device, parameters indicating a mode of operation of the imaging system. The imaging system interface module is configured to receive at least one of the parameters, to interpret such parameter and to allow the integrated system to assume a
(Continued)

mode of operation according the parameter. The integrated system further comprises a treatment tool interface module, configured to receive and detect a treatment event signal from a portable treatment tool. The treatment event signal indicates a treatment event, thereby allowing establishing a time of the treatment event and thereby establishing a locality of a treatment provided to the organ by the portable treatment tool.

26 Claims, 6 Drawing Sheets

(51) Int. Cl.
| | |
|---|---|
| *A61B 8/08* | (2006.01) |
| *A61B 8/12* | (2006.01) |
| *A61B 8/00* | (2006.01) |
| *A61B 5/00* | (2006.01) |
| *A61B 5/06* | (2006.01) |
| *A61B 6/12* | (2006.01) |
| *A61B 10/04* | (2006.01) |

(52) U.S. Cl.
CPC ............ *A61B 5/062* (2013.01); *A61B 5/7282* (2013.01); *A61B 5/7405* (2013.01); *A61B 5/7445* (2013.01); *A61B 6/12* (2013.01); *A61B 8/085* (2013.01); *A61B 8/0841* (2013.01); *A61B 8/12* (2013.01); *A61B 8/4254* (2013.01); *A61B 10/0233* (2013.01); *A61B 10/0241* (2013.01); *A61B 10/04* (2013.01); *A61B 2010/045* (2013.01)

(58) Field of Classification Search
CPC ... A61B 10/04; A61B 10/0233; A61B 5/0013; A61B 5/7445; A61B 5/7405; A61B 5/7282; A61B 5/062; A61B 5/0035; A61B 6/12; A61B 2010/045; G06T 19/003
See application file for complete search history.

(56) References Cited

U.S. PATENT DOCUMENTS

| | | | |
|---|---|---|---|
| 7,670,333 | B2 | 3/2010 | Schatzberger |
| 2004/0267121 | A1 | 12/2004 | Sarvazyan |
| 2008/0072151 | A1 | 3/2008 | Song |
| 2009/0048515 | A1 | 2/2009 | Suri |
| 2011/0149340 | A1 | 6/2011 | Lipman |
| 2014/0031718 | A1 | 1/2014 | Pastenak |

FOREIGN PATENT DOCUMENTS

| | | |
|---|---|---|
| EP | 1864624 | 12/2007 |
| WO | 2004002319 | 1/2004 |
| WO | 2004019799 | 3/2004 |
| WO | 2008063249 | 5/2008 |
| WO | 2009071766 | 6/2009 |
| WO | 2011161684 | 12/2011 |
| WO | 2012098483 | 7/2012 |

OTHER PUBLICATIONS

Lindseth, Ultrasound Guided Surgery: Multimodal Visualization and Navigation Accuracy, Dec. 2002.*
Chen et al., (1981) Shape context preserving deformation of 2D anatomical illustrations. Computer Graphics forum, pp. 1-12.

* cited by examiner

INTEGRATED SYSTEM FOR FOCUSED TREATMENT AND METHODS THEREOF

PRIORITY CLAIMS

The present application is a U.S. National Stage application of International Application PCT/IL2013/050065, filed on Jan. 24, 2013 by the inventors of the present application and titled: "Integrated System for Focused Treatment and Methods Thereof"; International Application PCT/IL2013/050065 claims the benefit of US Provisional Application No. 61/590,932, filed on Jan. 26, 2012; and International Application PCT/IL2013/050065 claims the benefit of U.S. Provisional Application No. 61/655,024, filed on Jun. 4, 2012; all of the aforementioned applications are hereby incorporated herein by reference in their entirety.

FIELD OF THE INVENTION

The invention, in some embodiments, relates to the field of integrated systems for facilitating local treatment in an organ, and more particularly, but not exclusively, to integrated systems capable of universally interfacing with other devices and systems.

BACKGROUND OF THE INVENTION

Treatment procedures and medical procedures performed on a body are commonly assisted by an imaging modality. Such treatment may include in some instances a diagnosis procedure, intended to collect information associated with the treated body. In some instances the treatment may include an intervention procedure such as a surgical procedure. Such intervention procedure is intended to intervene with the treated body, for example by removing material from the body or adding material or components thereto, manipulating body parts, for example to improve functionality, and so on.

Generally, an imaging modality used during a treatment procedure provides a user—for example a surgeon—a visible image corresponding to a selected region of the treated body, on a screen. Such an image is provided, in some instances and using some techniques, in real-time. Examples for real-time imaging during a treatment procedure are ultrasound imaging; some types of X-rays based imaging; CT; MRI; elastograph; and video imaging provided, for example, by a small CCD camera that is inserted to the treated body by catheterization and moved inside the body through a natural body conduit such as a blood vessel.

Many treatment procedures further employ a tracking system for example to facilitate localizing the treatment substantially only to a desired region of the treated body. A tracking system provides to a user, substantially in real-time, the location of an object, for example by providing a flow of data representing the three-dimensional (3D) location of the object as a function of time, relative to an origin of a pre-selected system of coordinates. The object may be for example a probe that is used for diagnostic purposes, e.g. a probe of an imaging modality. According to other examples an object which location is so provided substantially continuously may be a surgical instrument used for an intervention purpose, possibly inside the treated body, thereby not being directly seen by the user.

By considering the instantaneous location of a probe of the imaging modality (provided by the tracking system) and the location of the imaged region relative to the probe, assigning a position data to images of the imaging modality is enabled. Specifically, each pixel in the images may be assigned a 3D location along the pre-selected coordinates system mentioned above. Image data which is so assigned with image position data may further be employed for various objectives.

A virtual three-dimensional (3D) model of an organ which is subject to a medical procedure can be very helpful for the physician carrying out such procedure. Medical procedures that may be assisted by virtual 3D models are surgical procedures; intervening procedures employed for diagnostics purposes—for example Trans-Rectum Ultrasound (TRUS) imaging; and non-intervening procedures such as external inspection procedures.

In some instances a virtual 3D model may be generated from image data assigned with image position data as described above. Patent Application WO/2011/161684 (hereinafter '684) discloses embodiments of an integrated system configured to generate virtual 3D models from image data which is so assigned with image position data. A generated 3D model of an organ may be assigned a 3D position data relative to the patient's body—for example, relative to other organs of the body or to particular regions of the body that are easily identified—and may further be displayed to a user within a wider region of a body part. A 3D model of an organ which is so displayed may further be used and may assist for example in directing a treatment tool to the organ or to a region of the organ. Such integrated systems may further be used to virtually mark and store, on the model, regions that may be treated in the future or regions that were treated in the past, and even to associate with such marked regions of the organ past treatment results.

According to some embodiments disclosed in '684, such an integrated system as described above may be used to facilitate treatment which involves obtaining biopsy samples from a prostate. A treatment to a prostate suspected of having cancerous regions often involves obtaining several biopsy samples distributed within the prostate in a first session, and following inspection of the samples in a laboratory, providing a local treatment in a few or all of the sites from which samples were obtained, in a second session. Particularly, the system makes the locations of biopsy samples taken during a first session, visible to a surgeon during a subsequent treatment session. For example, a virtual 3D model of the prostate under treatment may be generated as described above, and the locations from which biopsy samples were obtained in the first session may be marked thereon. The model is stored in a computer's memory and pathology results of each biopsy sample may be virtually linked to the model at the location on the model from which each such biopsy sample was obtained. Since each biopsy sample location is individually identified, a physician is enabled to treat locations from which samples taken were shown by pathological analysis to be problematic, and has the option of not treating locations from which samples taken were shown to be healthy. Thus, during a second session, the virtual 3D model may be displayed on a screen together with a real-time image of the prostate and together with a real-time image of a treatment tool such as an ablation needle inserted into the prostate. By allowing the surgeon a simultaneous view of the desired treatment location (e.g. as a marked point on the virtual 3D model or on a live image) and the real-time location of the treatment tool as it is advanced towards the treatment location, local and focused treatment is facilitated and enabled.

SUMMARY OF THE INVENTION

Aspects of the invention, in some embodiments thereof, relate to integrated systems for facilitating local treatment in an organ. More specifically, aspects of the invention, in some embodiments thereof, relate to integrated systems capable to universally interface with other devices and systems.

As discussed above, an integrated system capable of providing to a user images (or other related data) obtained from an imaging modality and combined with image position data, may be an important tool, even essential, in the hands of the medical practitioner. Yet, it is often favorable for the medical practitioner to employ such an integrated system together with instrumentation that is already installed and is being used routinely by the practitioner. For example, for an urologist that uses an ultrasonography imaging system it may be highly desired to have such an integrated system as described above that could interface with the specific ultrasonography (US) imaging system which is currently being used. By interfacing the integrated system with the US system it is meant for example that the integrated system may be provided with image data substantially from that US system.

An integrated system that can so employ image data from an already available imaging modality is highly advantageous to the medical practitioner. One advantage is that such an integrated system should not necessarily be commercialized with an imaging modality. Thus, the cost of such an integrated system is expected to be considerably lower than the cost of an integrated system which comprises and is commercialized with an imaging modality. Second, the medical practitioner does not have to learn the details of operating a new imaging modality. From the practitioner point of view, the practice of obtaining images does not change due to employment of such an integrated system, and using it, or not, is a matter of choice.

In addition to receiving image data per-se from an imaging modality as described above, additional data may be received and considered by the integrated system, to allow accurate assignment of position data to the images. For example, a parameter indicating the scale of received images, e.g. in terms of millimeters per pixel or pixels per millimeters, should be considered by the integrated system to accurately assign position data to each pixel in the images. Yet additional data may be needed to enable additional functionality of the integrated system as is further described and explained below. Such parameters, specifying a current mode of operation of an imaging system, may not be directly available from the imaging modality through standard interface, e.g. electronically or digitally, for other systems such as the integrated system. However such parameters may be provided to a user through a user-interface device, a display for example, in a human-comprehensible format.

Imaging systems of different models and different manufacturers may display or otherwise provide to a user such parameters indicating current operating mode in different ways. By the integrated system being capable of universally interfacing with other instrumentation it is meant that the integrated system may interface with a same type of instrumentation of various models and various makes for effectively receiving required data. For example, the integrated system may interface with a US imaging system of any one of several models and several manufacturers, and obtain such operating-state indicating parameters therefrom.

Another example for universal interfacing with an already existing instrumentation involves a treatment tool used by the medical practitioner. As discussed above, the integrated system may be employed to record a location of a treatment site and to assist guiding a treatment tool to a recorded treatment site. For example, a location of a treatment site may be recorded during a first treatment session, and then displayed to a practitioner on a virtual 3D model so as to assist the practitioner guide a treatment tool therteto, during a second treatment session.

For example, in a first treatment session to a prostate suspected of having cancer, biopsy samples are taken from several locations in the prostate for examination. To record the locations from where biopsy samples were taken, the momentary location of the biopsy needle should be monitored, and the moment of taking the sample should also be recorded. Thus, to record a location of a treatment site, the integrated system is configured to receive a signal generated by the treatment tool and indicating a treatment event. The integrated system is configured to use such a signal to record the treatment event, even though such a signal may be different for treatment tools of the same type but of different models and of different manufacturers.

Thus, according to an aspect of some embodiments, there is provided an integrated system for facilitating local treatment in an organ, comprising a tracking system and a processing unit. The tracking system is configured to functionally associate with one or more tracking sensors and is configured to provide data of location and orientation of each such tracking sensor along pre-selected coordinates substantially in real time.

The processing unit is configured to receive image data from an imaging modality which comprises a probe, the probe having a fixed spatial relationship with a tracking sensor. For example, the tracking sensor may be fixedly attached onto the probe, thereby having established fixed spatial relationship thereto. The probe is configured to collect image data of physical objects, wherein the image data represents a region in space having a known spatial relationship with the location and orientation of the probe at the time the image data is collected. For example, image data collected by an ultrasound probe may correspond to a region in space having a known shape (typically resembles a fan) in a longitudinal or a transverse direction relative to the probe.

The processing unit is further configured to receive position data, corresponding to location and orientation of a tracking sensor, from the tracking system. The processing unit is further configured to assign image position data corresponding to position data of tracking sensor having fixed spatial relationship with the probe, such position data being received from the tracking system, to image data received from the imaging modality.

The integrated system further comprises at least one from the group consisting of an imaging system interface module and a treatment tool interface module. The imaging system is capable of presenting to a user, through a user-interface device, parameters associated with a mode of operation of the imaging system. The imaging system interface module is configured to receive at least one of the parameters from the user interface device or in parallel to the user interface device. The imaging system interface module is further configured to interpret at least one parameter and thereby to allow the integrated system assume a mode of operation according to at least one parameter so interpreted.

The portable treatment tool is configured to provide a focused and local treatment to an organ and has a known spatial relationship with a tracking sensor functionally associated with the tracking system. The treatment tool interface module is configured to receive an event signal from the portable treatment tool indicating a treatment event. Upon receiving the event signal, the processing unit functionally associated with the treatment tool interface module may establish a time of the treatment event and thereby establish a locality of a treatment provided to the organ by the portable treatment tool.

Aspects and embodiments of the invention are described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

Embodiments of methods and/or devices of the invention may involve performing or completing selected tasks manually, automatically, or a combination thereof. Some embodiments of the invention are implemented with the use of components that comprise hardware, software, firmware or combinations thereof. In some embodiments, some components are general-purpose components such as general purpose computers. In some embodiments, some components are dedicated or custom components such as circuits, integrated circuits or software.

For example, in some embodiments, some of an embodiment is implemented as a plurality of software instructions executed by a data processor, for example which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Figure 1:
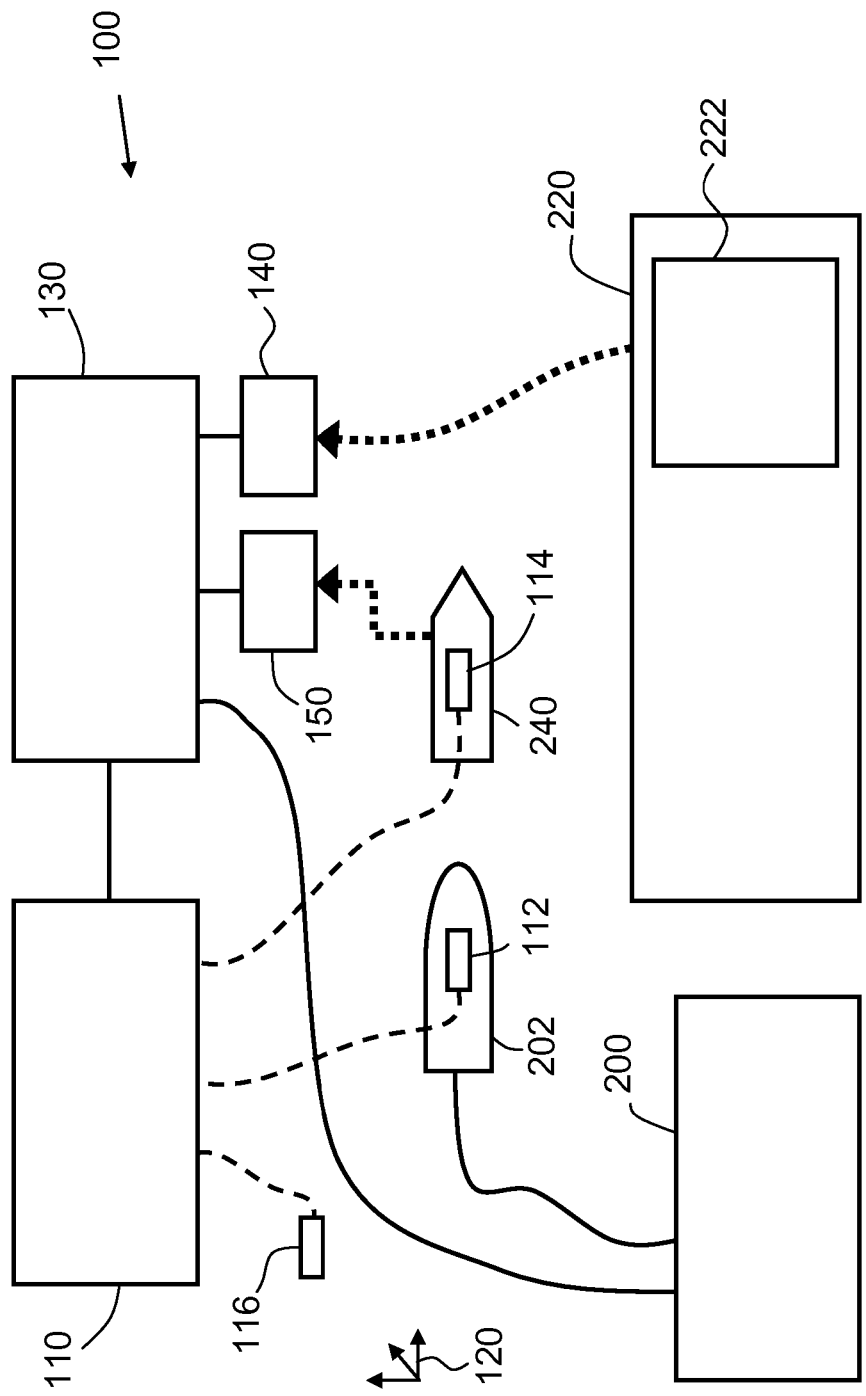
FIG. 1 schematically depicts an embodiment of an integrated system for facilitating local treatment in an organ, according to the teachings herein.

FIG. 1 schematically depicts an embodiment of an integrated system 100 for facilitating local treatment in an organ, according to the teachings herein. Integrated system 100 comprises a tracking system 110. Tracking system 110 is configured to functionally associate with one or more tracking sensors and to calculate and report the positions of such tracking sensors. Tracking system 110 is functionally associated with a first tracking sensor 112, with a second tracking sensor 114 and with an optional tracking sensor 116. Tracking system 110 is further configured to calculate and provide the location and orientation of first tracking sensor 112, of second tracking sensor 114 and of optional tracking sensor 116 along a pre-selected coordinate system 120, substantially in real time.

According to some embodiments, tracking system 110 comprises an electromagnetic field generating device (not shown) generating an electromagnetic (EM) field having a known magnitude and direction in substantially every point in a working space. For example, a set of field generating coils (not shown) may be firmly attached to a bed configured to support a patient during a treatment procedure. The generating coils generate an EM field having known magnitude and direction around the bed, and particularly around and inside the body of a patient supported on the bed. A tracking sensor functionally associated with tracking system 110, for example first tracking sensor 112, is configured to detect and provide, substantially instantaneously, the magnitude and direction of the EM field, substantially at the position of first tracking sensor 112. Likewise, second tracking sensor 114 is configured to detect and provide, substantially instantaneously, the magnitude and direction of the EM field, substantially at the location of second tracking sensor 114. According to some embodiments each tracking sensor comprises a coil or a set of coils (not shown), and the amplitudes of the signals resulting from the EM field received in each of the coils in the set of coils indicate the location and orientation of the sensor. Each tracking sensor is electronically associated with tracking system 110, for transmitting the data received by the tracking sensor. Such an electronic association between the tracking sensors and tracking system 110 may be accomplished by wires in some embodiments, and may be wireless in some embodiments.

By considering the instantaneous data of magnitude and direction of the EM field at the location of a tracking sensor, the instantaneous location of the sensor relative to the EM field generating coils is calculated by tracking system 110. The location of the tracking sensors may further be provided to a user in terms of 3D coordinates data relative to coordinate system 120. An example of a commercially available tracking system as is described herein is 3D Guidance trakSTAR™ by Ascension Technology Corporation.

Integrated system 110 further comprises a processing unit 130, functionally associated with tracking system 110 for receiving real-time position data of tracking sensors functionally associated with tracking system 110. Processing unit 130 is further configured to functionally associate with an imaging modality 200 for receiving image data therefrom. Imaging modality 200 is functionally associated with an imaging probe 202 configured to collect image data of physical objects, wherein the image data corresponds to a region in space having a known spatial relationship with the location and orientation of imaging probe 202 at the time the image data is collected. An exemplary imaging modality is an ultrasonography system comprising a portable probe comprising ultrasonic (US) transducers (referred to herein as a US probe), as is known in the art of medical imaging. The US probe transmits ultrasonic waves in a beam having a typical shape e.g. of a fan, and receives echoes from objects that are present in the range of the beam and reflect back the ultrasonic waves. The echoes are processed and may be transformed into image data and further into an image wherein every pixel in the image substantially corresponds to a particular point in space, within the range of the ultrasonic beam at the time the image data is collected.

First tracking sensor 112 is firmly attached to imaging probe 202, thereby establishing a fixed spatial relationship between imaging probe 202 and first tracking sensor 112. Thus, position data (comprising location and orientation along coordinate system 120) of first tracking sensor 112 is attributed also to imaging probe 202. Processing unit 130 receives image data, collected by imaging probe 202, from imaging modality 200, and substantially simultaneously receives position data, generated by first tracking sensor 112 and attributed to imaging probe 202, from tracking system 110. Processing unit 130 further considers the known spatial relationship between the location of imaging probe 202 and the region in space from which image data is collected by the probe. Thereby, processing unit 130 assigns image data received from imaging modality 200, with image position data corresponding to the instantaneous location of imaging probe 202. Assigning to image data image position data means herein that substantially every pixel in an image corresponding to the image data may be assigned a position along 3D coordinate system 120.

The known spatial relationship between the location of imaging probe 202 and the region in space from which image data is collected by the probe, generally depends on a few factors. A few such factors are constant. One such constant factor may be the technology associated with the specific imaging modality being employed. For example, an image obtained using an ultrasound probe of an ultrasonography modality relates to the probe differently compared, for example, with an MM 2D image obtained using an MRI device. Another factor may be the manufacturer of the imaging modality and the specific model thereof. For example, various US probes of different manufacturers and different models may generally have different beams, having different spatial relationship with the generating probes. For accurately assigning image position data to image data received from imaging modality 200, a user may thus provide to processing unit 130 the relevant factors associated with the imaging modality being currently employed. For example, in an integrated system 100 configured to optionally receive image data from any US imaging modality named in a list—a user may provide an indication to processing unit 130 which imaging modality from the list is currently selected for use, so that processing unit 130 may thereafter accurately assign image position data to image data received from the US imaging modality, as described above.

The spatial relationship between the probe and the region in space from which image data is collected, may further depend on additional factors, which, in contrast to the factors mentioned above, are not constant and may change in time, possibly by a user while operating the imaging modality. For example, while operating an US imaging modality, the user may change a scale of an image displayed on a screen, e.g. change the number of pixels per millimeter in the image; or change a mode of view, for example from a longitudinal view to a transverse view; or select "freeze" mode to freeze the image on the screen; and so on. It may be desired therefore to take into account such factors also, to be able to assign correctly image position data to image data.

Parameters indicating the mode of operation of an imaging modality—parameters such as the scale of the current image, mode of view, etc.—may not be directly available from the imaging modality through standard interface, e.g. electronically or digitally, for other systems such as integrated system 100. However such parameters may be provided to a user through a user-interface device, a display for example, in a human-comprehensible format. For example, the scale of a current US image may be displayed on a screen of the imaging modality, together with the image itself. A currently selected mode of view may be indicated by a word or a letter or a graphical symbol, on the screen showing the image or on a separate screen of the same imaging modality or using an indicating light that turns on, and so on.

FIG. 1 schematically depicts an imaging system 220, capable of presenting to a user, through a user interface device 222 and in a user-comprehensible format, parameters that indicate a mode of operation of imaging system 220. In some embodiments user interface device 222 may be a screen displaying to a user such parameters in a user comprehensible format; in some embodiments user interface device 222 may be a control board providing to a user visual indications of such parameters e.g. using lights that turn on and off; in some embodiments user interface device 222 may be a loudspeaker providing to a user sound indications; or a combination of such user interface devices; and so on.

Integrated system 100 further comprises an imaging system interface module 140, functionally associated with processing unit 130. Imaging system interface module 140 is configured to functionally associate with imaging system 220 for receiving at least one parameter indicating a mode of operation of the imaging system. According to some embodiments imaging system interface module 140 is configured to receive such parameters from user interface device 222. For example, in embodiments where user interface device 222 comprises a screen (not shown), imaging system interface module 140 may comprise an image acquiring device such as a camera to obtain images of the screen. In such embodiments the camera is aligned so as to capture images of the screen of the user interface device. Additionally, imaging system interface module 140 may comprise an image processing module configured to process such screen images to obtain the required parameters therefrom. In embodiments where user interface device 222 comprises a control board as described above, imaging system interface module 140 may comprise a light sensitive device configured to detect indicating lights that turn on and off. In embodiments where user interface device 222 comprises a loudspeaker, imaging system interface module 140 may comprise a microphone electrically associated with an amplifier to detect indicative sound signals from the loudspeaker of user interface device 222.

According to some embodiments imaging system interface module 140 is configured to receive such parameters in parallel to user interface device 222. For example, in embodiments where user interface device 222 comprises a screen, imaging system interface module 140 may electrically interface in parallel to a video input connector of the screen, to receive the video signals that generate images on the screen.

Upon receiving from imaging system 220 a parameter or parameters indicating a mode of operation of imaging system 220 as described above, imaging system interface module 140 is further configured to interpret such parameters and to allow integrated system 100 to assume a mode of operation according to the interpreted parameters, as is further explained and exemplified further below.

According to some embodiments, integrated system 100 is configured to facilitate local treatment of an organ using a portable treatment tool 240, configured to provide a focused and local treatment to the organ.

Second tracking sensor 114 is firmly attached to portable treatment tool 240, thereby establishing a known spatial relationship between portable treatment tool 240 and second tracking sensor 114. Thus, position data (comprising location and orientation along coordinate system 120) of second tracking sensor 114 may be attributed also to portable treatment tool 240. Processing unit 130 receives from tracking system 110 a substantially continuous stream of position data of second tracking sensor 114, and may thus record, e.g. in a computer's memory, the position (location and orientation) of portable treatment tool 240 as a function of time.

Having the varying location of portable treatment tool 240 recorded as a function of time, registering a location of a particular focused and local treatment requires establishing the time of the treatment event. For example, portable treatment tool 240 may comprise a biopsy gun (not shown) for obtaining a biopsy sample from an organ of a patient. For recording the location in the patient's body from which a biopsy sample is taken, the time of activating the biopsy gun to take the biopsy sample should be established.

Thus, integrated system 100 comprises a treatment tool interface module 150, configured to functionally associate with portable treatment tool 240. Treatment tool interface module 150 is configured to receive and detect a treatment event signal from portable treatment tool 240, indicating a treatment event. Upon receiving and detecting such a signal indicating a treatment event by treatment tool interface module 150, processing unit 130 may establish a time of the treatment event and thereby establish a locality of the treatment provided to the organ by portable treatment tool 240. Establishing the locus of the treatment may be accomplished for example by correlating the time of the treatment event with the time-dependent location of portable treatment tool 240 mentioned above.

Figure 2:
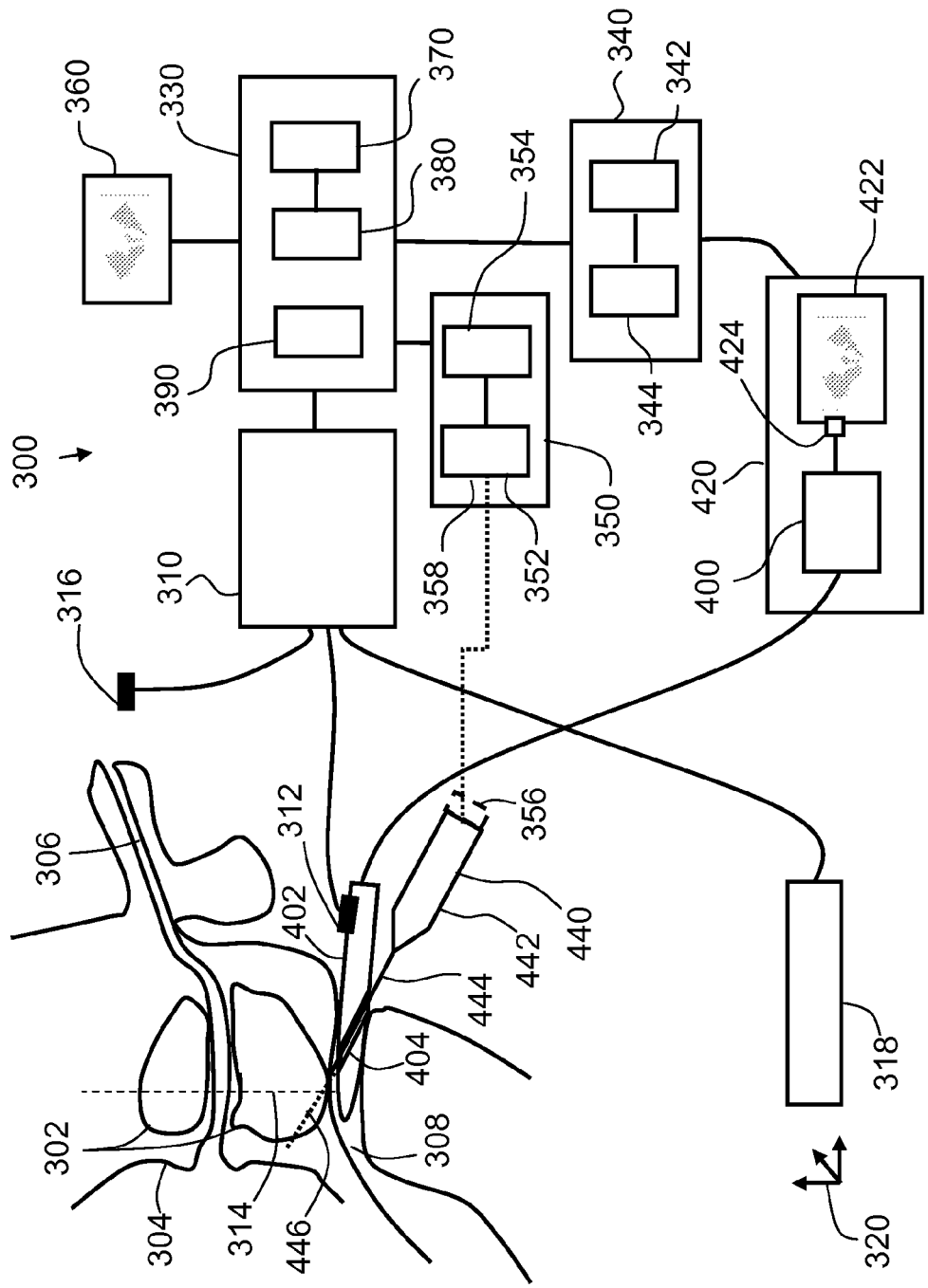
FIG. 2 schematically depicts an embodiment of an integrated system for facilitating local treatment in a male's prostate according to the teachings herein.

FIG. 2 depicts schematically an embodiment of an integrated system 300, for facilitating local treatment in a male's prostate according to the teachings herein.

Genitourinary anatomy of a male's body under treatment is sketched on the upper left of FIG. 2, showing the prostate 302, bladder 304, urethra 306, and rectum 308. An ultrasonography imaging system 420 is in use, comprising ultrasound scanner 400 functionally associated with a transrectal ultrasound (TRUS) transducer 402 placed in rectum 308. Imaging system 420 further comprises an imaging system screen 422. Ultrasound scanner 400 is configured to provide an ultrasound image obtained from ultrasound image data collected by TRUS transducer 402 and to display such image on imaging system screen 422. In longitudinal mode, TRUS transducer 402 is configured to collect image data from a plane that includes the longitudinal axis of TRUS transducer 402 (e.g. the plane of FIG. 2). In transverse mode, TRUS transducer 402 is configured to collect image data in a plane 314 perpendicular to the longitudinal axis of TRUS transducer 402. Further, TRUS transducer 402 may be positioned at a series of sequential positions along rectum 308, and collect at each such position an image data corresponding to a plane substantially parallel to plane 314 and cross-sectioning prostate 302, thereby obtaining a series of two-dimensional (2D) images.

Integrated system 300 comprises an electromagnetic tracking system 310, configured to obtain, substantially in real time, the spatial location of one or more tracking sensors relative to the origin of a pre-selected coordinate system 320. Tracking system 310 includes a transmitter 318 that produces a local electromagnetic field. Tracking system 310 is functionally associated with a first tracking sensor 312 firmly attached to TRUS transducer 402, thereby establishing a fixed spatial relation with TRUS transducer 402. According to some embodiments, an optional tracking sensor 316, substantially similar to first tracking sensor 312, may be attached to an identifiable location of the treated body, for example L5 vertebra. Each tracking sensor functionally associated with tracking system 310 is configured to sense the EM field generated by transmitter 318 at the location of the tracking sensor, and to obtain a signal corresponding to the sensed EM field. Upon receiving such signals from each tracking sensor, tracking system 310 calculates the spatial location and angular orientation of the tracking sensor, relative to the location of transmitter 318, and thereby relative to coordinates system 320.

Integrated system 300 further comprises main controller 330, functionally associated with tracking system 310 and with imaging system 420 for receiving US image data collected by TRUS transducer 402. Integrated system 300 also comprises integrated system display 360, functionally associated with main controller 330. Main controller 330 is configured to receive ultrasound image data from imaging system 420, and to display corresponding US images on integrated system display 360. Main controller 330 is also configured to receive location and orientation data of first tracking sensor 312 and optional tracking sensor 316 from tracking system 310. Using the known spatial relationship of the region from which image data is collected to the location of TRUS transducer 402 at the time the image data is collected according to the teachings herein, main controller 330 is further configured to assign position data to the received ultrasound images. Assigning position data to the received ultrasound images means that substantially each pixel in an ultrasound image obtained from the image data, is assigned a location in coordinates system 320 as is detailed and explained above.

According to some embodiments, optional tracking sensor 316 is attached to an identifiable location on the treated body of the patient and thereby moves together with the treated body. According to some embodiments, main controller 330 is configured to consider position data obtained from optional tracking sensor 316 and employ such position data to assign to image data position data along a coordinate system attached to the treated body. For example, by subtracting the instantaneous location of optional tracking sensor 316 along coordinates system 320 from the instantaneous location of first tracking sensor 312 along the same coordinates system, main controller 330 may obtain a location of first tracking sensor 312 relative to the location of optional tracking sensor 316, thereby eliminating or at least reducing effects of body movements on position data assigned to image data of the ultrasound images.

TRUS transducer 402 is equipped with a needle guide 404 for the insertion of a portable treatment tool 440 such as a biopsy gun 442 comprising a biopsy needle 444. When biopsy gun 442 is suitably placed in needle guide 404, biopsy gun 442 and biopsy needle 444 are confined to displacements only along a straight trajectory 446. According to some embodiments a second tracking sensor 314 (not shown in FIG. 2) is firmly attached to biopsy gun 442, thus allowing main controller 330 to continuously register position data of biopsy gun 442 in all three dimensions as a function of time. However, in some instances it is not desired to have biopsy gun 442 attached to second tracking sensor 314, particularly if second tracking sensor 314 is connected by wires to tracking system 310 for transmitting positions signals. Consequently, in instances where biopsy gun 442 is not attached to second tracking sensor 314, registering the instantaneous location of biopsy gun 442 and biopsy needle 444 may be accomplished as described below.

When biopsy gun 442 is suitably placed in needle guide 404, biopsy gun 442 has a partly-known spatial relationship with first tracking sensor 312, and consequently, the instantaneous location of biopsy gun 442 may be registered by main controller 330. Furthermore, when biopsy gun 442 is suitably placed in needle guide 404 and is used as described above, the location of biopsy needle 444 is also known at least in two dimensions, namely in the plane perpendicular to the long axis of the needle, coinciding with trajectory 446. In the routine course of a prostate biopsy sampling assisted by US imaging, the surgeon may choose to position the biopsy gun at any arbitrary position along needle guide 404. When biopsy gun 442 is so placed in needle guide 404 and is arbitrarily displaced along needle guide 404 by the surgeon, spatial relationship between biopsy gun 442 and first tracking sensor 312 is known only partly. In other words, position data obtained from first tracking sensor 312 may be employed to determine the location of biopsy needle 444 only in the plane perpendicular to the needle axis. The location of biopsy needle 444 in the third dimension, namely along trajectory 446, is obtained by methods described further below.

The correspondence of the image data obtained from TRUS transducer 402 to the location of TRUS transducer 402 depends on the mode of operation of US imaging system 420. In the routine course of operating TRUS transducer 402, the surgeon may select one of several modes of operation to obtain a desired US image. For example, the surgeon may select a desired X scale and a desired Y scale, corresponding to the scale of the US image along the X and Y axes, respectively. Further, with some types of a "side fire" TRUS transducer, a longitudinal mode (sometime referred to as "sagittal" mode) may be selected, providing a US image corresponding to a plane including the long axis of TRUS transducer 402. Additionally or alternatively a transverse mode may be selected, providing a US image corresponding to a plane perpendicular to the long axis of TRUS transducer 402. In some types both longitudinal mode and transverse mode may be activated simultaneously and a corresponding longitudinal view and a transverse view are displayed side by side on imaging system screen 422. With some types of TRUS transducers, particularly with "end fire" transducers, the surgeon may select to "flip" the US image, thereby obtaining a vertically mirrored image on imaging system screen 422.

The mode of operation of US imaging system 420 and particularly the associated details of the US image displayed on imaging system screen 422 may not be directly available, through conventional electrical or digital interface, to integrated system 300. However, according to some embodiments, such details of modes of operation of US imaging system 420 are displayed to the user on imaging system screen 422, in a human-comprehensible format. The exact format of presentation of such details, while being comprehensible to the experienced user, may vary significantly from one model of US imaging system 420 to another model, and from a US imaging system manufactured by one vendor to another US imaging system manufactured by another vendor.

Integrated system 300 thus comprises an imaging system interface module 340, functionally associated with US imaging system 420 for receiving video signals associated with images displayed on imaging system screen 422. According to some embodiments imaging system interface module 340 receives such video signals by connecting electrically to a video input connector 424 of imaging system screen 422 thereby receiving such video signals in parallel to imaging system screen 422.

Imaging system interface module 340 comprises a library 342 including a list of commercially available ultrasound imaging systems. The list consists of the US imaging systems that integrated system 300 are configured to functionally associate with for the purpose of obtaining parameters indicating a mode of operation of a selected US imaging system, and correspondingly assuming a mode of operation of integrated system 300. For each US imaging system in the list, one or more screen images associated with respective one or more modes of operation of the US imaging system, are specified and registered in library 342, as is further exemplified and explained below. Imaging system interface module 340 further comprises an image processing module 344, configured to process and analyze the video signals received from imaging system 420 and reconstruct associated screen images from the received video signals. Image processing module 344 is further configured to compare such reconstructed screen images associated with the received video signals, with the screen images that are specified in library 342 for the selected US imaging system, to obtain the parameters indicating the mode of operation of US imaging system 420.

Figure 3A:
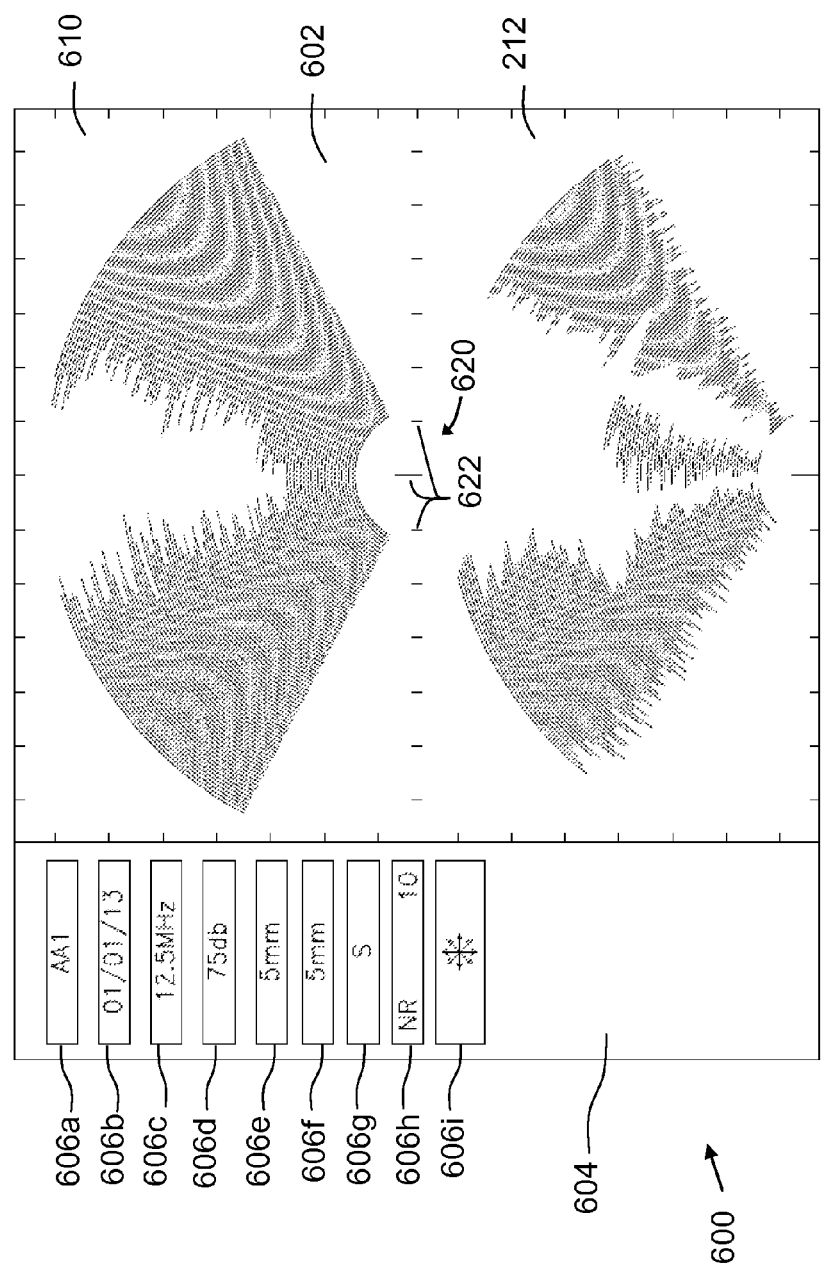
FIGS. 3A and 3B schematically illustrate two exemplary screen images, respectively, of two different US imaging systems, respectively.
Figure 3B:
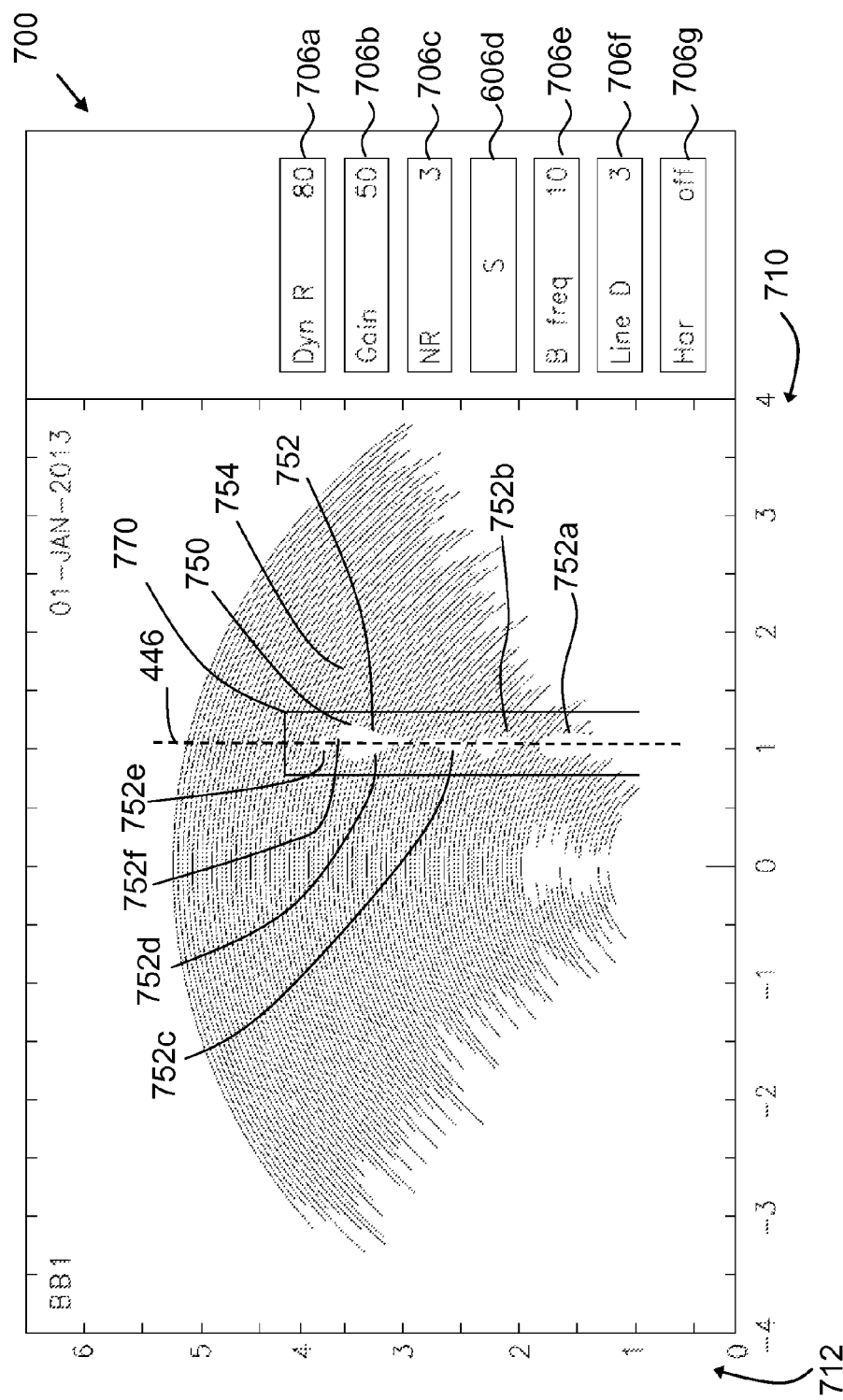

Embodiments of a method for obtaining such parameters by imaging system interface module 340 are further detailed and explained using FIGS. 3A and 3B. FIG. 3A illustrates schematically an exemplary screen image 600 of a US imaging system 420A from a particular vendor AA and of a particular model AA1. Furthermore, screen image 600 is displayed to a user (on imaging system screen 422 of US imaging system 420A) when US imaging system 420A is operating in a particular mode of operation. Imaging system interface module 340 (in FIG. 2) receives the video signals associated with screen image 600 and thereby virtually reconstructs screen image 600 for processing and analysis.

Screen images of US imaging system 420A have a typical general view comprising a right field 602 for the US image and a left field 604 for displaying to a user operation data and parameters indicating the selected mode of operation of the imaging system. For example, box 606a in left field 604 indicates the model AA1 of imaging system 420A; box 606b indicates the current date; and so on. According to some embodiments, a user of integrated system 300 indicates to imaging system interface module 340 the particular US imaging system 420A by selecting a name identifying US imaging system 420A in the list in library 342. Upon such selection being made, image processing module 344 compares screen image 600, or selected portions thereof, to respective portions in each screen image associated with US imaging system 420A specified in library 342. For example, by comparing a portion of screen image 600 comprising box 606e, to a respective portion in library-stored screen images, image processing module 344 identifies the X-scale parameter of the US image in right field 602 of screen image 600 to be 5 mm between tic marks; by comparing a portion of screen image 600 comprising box 606f to a respective portion in library-stored screen images, image processing module 344 identifies the Y-scale of the US image to be 5 mm between tic marks; by comparing a portion of screen image 600 comprising box 606g to a respective portion in library-stored screen images, image processing module 344 identifies that right field 602 displays a split view, comprising a longitudinal image 610 above and a transverse image 612 below. Alternative or additional methods for identifying operational parameters of imaging system 420A from screen image 600 are also contemplated. For example, according to some embodiments image processing module compares central portion 620 of right field 602 to detect tic marks 622 identifying a split view.

FIG. 3B illustrates schematically an exemplary screen image 700 of a US imaging system 420B from a vendor BB (different from vendor AA) and of a particular model BB 1. Further, screen image 700 is displayed to a user (on imaging system screen 422 of US imaging system 420B) when US imaging system 420B is operating in a particular mode of operation. Using the method described above, a user of integrated system 300 selects a name identifying US imaging system 420B in the list in library 342. Consequently, image processing module 344 compares screen image 700, or selected portions thereof, to each screen image specified in library 342 and associated with US imaging system 420B. For example, screen images of US imaging system 420B indicate the X scale and Y scale of the current US image by numerals positioned proximate to tic marks of the axes of the US image. Thus, image processing module 344 is programmed to compare X axis region 710 to identify the X scale of the US image to be 1 cm per two tic marks; likewise, image processing module 344 is programmed to compare Y axis region 712 to identify the Y scale of the US image to be 1 cm per two tic marks. Further, image processing module 344 compares a portion of screen image 700 comprising box 706d to identify the US image as a sagittal (longitudinal) view. By employing similar methods of image processing and images comparison, additional operational parameters and viewing parameters of the particular imaging system 420 in use may be identified. Operational modes that imaging system interface module 340 is configured to identify according to some embodiments include also: freeze mode, wherein the US image is frozen, namely is not continuously refreshed; flipped screen, wherein the US image is mirrored along a vertical axis; and multiple view such as a dual view, wherein two or more US images are displayed simultaneously on the screen.

As explained above, imaging system interface module 340 is thus configured to obtain parameters that identify the specific operational mode of imaging system 420 corresponding to each received US image. Using the parameters so obtained by imaging system interface module 340, main controller 330 establishes the spatial relationship between the momentary location of TRUS transducer 402 and the region in space from which the US image data was collected by the transducer. Using the correspondence of the image data to the location of TRUS transducer 402 at the time the image data is collected, main controller 330 assigns position data to the received ultrasound images.

Image data assigned with image position data as described above may be further employed to obtain various objectives, for example as detailed and explained in patent application '684. According to some embodiments a user may obtain a series of US images along planes substantially parallel to one another and slightly displaced from one another. For example, as depicted schematically in FIG. 2, by operating TRUS transducer 402 in transverse mode and displacing TRUS transducer 402 along the rectum, a user may obtain a series of images along slightly displaced planes cross-sectioning prostate 302 and substantially parallel to plane 314. Main controller 330 may then assign image position data to the image data, e.g. as described above. Using the assigned position data to each pixel in the images, the obtained 2D images may be arranged together to obtain a 3D image of the scanned region, for example as a three dimensional matrix, wherein each pixel of a 2D image is a voxel (a volumetric pixel) of the 3D image. A voxel of such a 3D ultrasound image may correspond to a volume in space having typical lateral dimension of about 0.2 mm. A 3D image of the prostate—or of any other organ—may be used to obtain further information. According to some embodiments main controller 330 is configured to obtain from such an available 3D image of an organ, a 2D image corresponding to a cross-section of the organ along an arbitrarily selected plane, by employing suitable image-processing-derived techniques well known in the art.

According to an aspect of some embodiments, 2D images assigned with image position data may further be used to assist generation of a virtual 3D model of an imaged organ, e.g. a prostate. According to some embodiments, main controller 330 is configured to employ methods for generation of virtual 3D models of an organ, for example such as disclosed in detail in application '684. According to some embodiments a user may select a few US images of the organ, e.g. one image obtained in sagittal mode and one image obtained in transverse mode. When an image is displayed on integrated system display 360, the user may virtually mark selected points of the border line of the prostate in the displayed image. Each such virtual point is assigned a location along the same coordinates assigned to the US image. A 3D modeling module 370 in main controller 330 then uses a generic virtual 3D model of the prostate, initially stored in memory, to construct the virtual 3D model of the specific imaged prostate. The generic virtual 3D model is transformed, e.g. by such transformations as displacement, rotation and expansion, so as to fit best the points marked by the user. The resulting virtual model is used as a virtual 3D model of the prostate.

According to some embodiments, a virtual 3D model of the prostate may be generated by surface meshing a multitude of points marked on a series of 2D images of the prostate. A series of substantially parallel images, or roughly parallel images, e.g. such that were previously obtained in transverse mode by displacing TRUS transducer 402 along the rectum, are considered. For each image, when displayed on integrated system display 360, the user may virtually mark a multitude of points on the border line around the prostate. 3D modeling module 370 of main controller 330 then employs surface meshing techniques known in the art to generate a single mesh that includes all the marked points of all the considered images, thereby generating a virtual 3D model of the prostate.

According to some embodiments main controller 330 further comprises a 3D registration module 380 for manipulating and registering image data and image position data as described below.

According to some embodiments, 3D registration module 380 is configured to virtually mark, on a virtual 3D model generated by 3D modeling module 370, a mark corresponding to a designated point along a 3D coordinate system. For example, on a US image displayed on integrated system display 360 and already assigned with image position data, as described above, a user may virtually mark a designated point, e.g. by graphically marking the point on a screen of integrated system display 360. Such a marked point may then be assigned a corresponding 3D location determined by the plane of the US image and the position of the point within the plane. In other words, the marked point may be assigned the same position data assigned to the pixel of the US image which is closest to the marked point. Then, a point having the same coordinates may be virtually marked on a virtual 3D model of the organ imaged by the US image.

In some embodiments a designated location to be marked on a virtual 3D model may be provided as a record of a location along a 3D coordinate system. In some embodiments such a record is provided as a triplet of values indicating location along three coordinates. In some embodiments, a designated location to be marked may be a treatment location, defined as a location of a treatment event, as is described in detail further below. For example, obtaining a biopsy sample from a prostate treated by integrated system 300 may be in some embodiments a treatment event, whereas the location of the distal tip of the biopsy needle is the treatment location. According to some embodiments, a region from which a biopsy sample was collected, may be registered and marked on a virtual 3D model by registration module 380.

According to some embodiments 3D registration module 380 may map a first set of image data assigned with image position data along a first coordinate system, onto a second set of image data assigned with image position data along a second coordinate system. Mapping one set of data onto a second set of data herein means transforming at least one of the coordinate systems e.g. by translation and rotation, so as to obtain a fit between the two sets of data. For example, image data, substantially of a same organ, may be obtained in two different treatment sessions, in two different times and even using two different sets of instrumentation. Subsequently, position data assigned to a same anatomical detail or anatomical landmark of the organ may be different in images obtained during the two treatment sessions. A virtual 3D model generated using the first set of image data, would be similar in shape to a virtual 3D model generated using the second set of image data. However position data assigned to each of the virtual 3D models may be different, whereas the differences consist substantially of translation and rotation between the two coordinate systems. According to some embodiments, 3D registration module 380 is configured to receive a first virtual 3D model of an organ, with corresponding position data along a first pre-selected set of coordinates. 3D registration module 380 is further configured to receive a second virtual 3D model of the organ, with corresponding position data along a second pre-selected set of coordinates. 3D registration module 380 is yet further configured to transform at least one of the pre-selected set of coordinates of first virtual 3D model and the pre-selected set of coordinates of the second virtual 3D model, using shape-preserving transformations such as translation and rotation, so as to obtain a best fit between the first virtual 3D model and the second virtual 3D model. By so transforming one set of image data to fit another set of image data, all data assigned with position data along the first set of coordinates may be assigned with position data along the second set of coordinates. Consequently, both sets of image data may be visually displayed together along a same coordinate system.

According to some embodiments the first virtual 3D model and the second virtual 3D model may be obtained from data received from a same imaging modality. For example, the two sets of image data may be obtained from two different sessions of biopsy sampling under US imaging. According to some embodiments the first virtual 3D model and the second virtual 3D model are obtained from data received from two different imaging modalities, respectively. For example the first set of image data may be obtained from an ultrasound imaging modality and the second set of image data may be obtained from an MM apparatus.

According to some embodiments, the first set of image data and the second set of image data may comprise data from 2D images received substantially from an imaging modality such as imaging modality 200 in FIG. 1 or US scanner 400 in FIG. 2. According to some embodiments a first 3D image is generated from the first set of 2D images of an organ, and a second 3D image is generated from the second set of 2D images of the same organ, as described above. According to some embodiments, 3D registration module 380 is configured to receive the first 3D image of an organ, with corresponding position data along a first pre-selected set of coordinates. 3D registration module 380 is further configured to receive the second 3D image of the organ, with corresponding position data along a second set of coordinates. 3D registration module 380 is yet further configured to transform at least one of the pre-selected set of coordinates of first 3D image and the pre-selected set of coordinates of the second 3D image, using shape-preserving transformations such as translation and rotation, so as to obtain a best fit between the first 3D image and the second 3D image. By so transforming one coordinate system relating to a first set of image data to fit another coordinate system relating to a second set of image data, all data assigned with position data along the first set of coordinates may be assigned with position data along the second set of coordinates. Consequently, both sets of image data may be visually displayed together aligned to a same coordinate system.

According to some embodiments the first 3D image and the second 3D image may be obtained from a same imaging modality. For example, the two sets of image data may be obtained from two different sessions of biopsy sampling assisted by US imaging. According to some embodiments the first 3D image and the second 3D image are obtained from two different imaging modalities, respectively. For example the first set of image data may be obtained from an ultrasound imaging modality and the second set of image data may be obtained from an MM apparatus.

As discussed above, in some instances when biopsy gun 442 is in use, it is not desired to attach the biopsy gun to second tracking sensor 314, particularly if second tracking sensor 314 is connected by wires to tracking system 310. In such instances, and when biopsy gun 442 is suitably placed in needle guide 404 of TRUS transducer 402, the location of biopsy gun 442 is known along two dimensions, namely in the plane perpendicular to trajectory 446 (coinciding with the axis of biopsy needle 444). In some embodiments the location of biopsy needle 444 along trajectory 446 is detected as discussed below.

Reference is made again to FIG. 3B, schematically depicting US image 700 obtained by a TRUS transducer such as TRUS transducer 402, comprising a needle guide 404, in sagittal mode. In sagittal mode the ultrasound beam overlaps with trajectory 446 of biopsy needle 444, hence biopsy needle 444 may appear in the image along an a-priori known region of the image. Trajectory 446 may thus be constantly displayed on the image e.g. by a suitable synthetic video signal.

When a typical biopsy gun is activated to collect a biopsy sample, the biopsy needle advances forward very rapidly and within less than a second retracts back, with a sample tissue in the needle notch. In typical biopsy guns the time from releasing the needle until the needle retracts back may be even about 200 mSec. At a typical refresh rate of screen images of a US scanner of about 15 Hz, about three sequential images may include a view of the biopsy needle during the sampling event.

Figure 4:
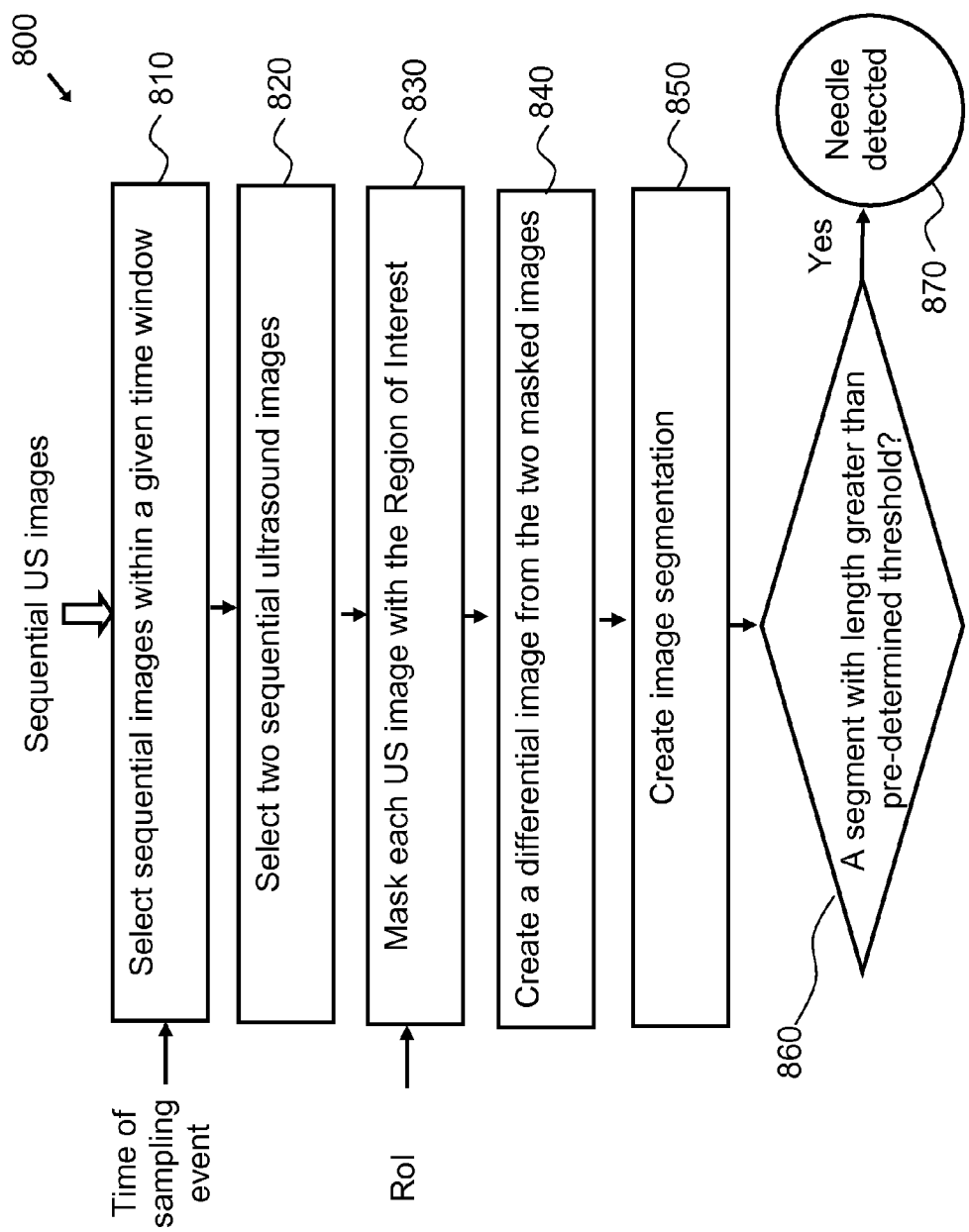
FIG. 4 schematically depicts an embodiment of a method for detecting and image of a biopsy needle in an ultrasound image, and FIG. 5 schematically depicts an embodiment of a method for detecting a treatment event such as obtaining a biopsy sample using a biopsy needle, by a treatment tool interface module, according to the teachings herein.

Image 700 comprises an image 750 of a released biopsy needle. Image 750 comprises several stains 752 brighter than the surroundings 754 and spread roughly along trajectory 446 on image 700. According to some embodiments, main controller 330 in FIG. 2 comprises a needle detection module 390 configured to detect an image of a needle in an ultrasound image, along a pre-defined region of the ultrasound image, by employing techniques of image processing. FIG. 4 schematically illustrates an embodiment of a method 800 for needle image detection in an US image. In step 820 two sequential US images are selected. In step 830 a region of interest is selected in each image by masking the image with an image mask, having a window in the region of interest. The region of interest is a stripe of pixels 770 in FIG. 3B, stretching along trajectory 446. According to some embodiments, masking an image with a mask comprising a window may be represented mathematically as follows: the US image is represented by a matrix M having rows and columns equal in number to the lines and pixels in a line, respectively, in the image. Thus, each pixel of the image is represented by one element of the matrix. The mask is represented by a matrix K of similar dimensions as M, wherein elements inside stripe 770 have a value of 1 and elements outside stripe 770 have a value of 0. Masking is accomplished by obtaining a matrix R wherein each element rij of R is a multiplication of an element of M with a respective element of K $r_{ij}=m_{ij} \cdot k_{ij}$. The resulting matrix has elements representing the US image inside the region of interest, and 0's elsewhere. In step 840 the difference between the two masked images is obtained. When neither of the two sequential US images a biopsy needle, the differences between the two sequential images are relatively minute. When a biopsy needle is activated, then, due to the rapid displacement of the needle, the needle would be fully seen, or almost fully seen, in one image, whereas it would be absent, or almost absent, from the other image. Thus, a significant difference between the images along the region of interest may indicate the presence of an activated needle. In step 850 the region of interest is analyzed to identify segments having brightness higher than the surroundings, thereby identifying stains 752. In step 860 the size of identified stains is estimated substantially along the direction of trajectory 446. According to some embodiments, a single stain having a length greater than a pre-determined length $l_0$ indicates, in step 870, the presence of a biopsy needle in the US image. According to some embodiments a number of stains—each stain greater than $l_0$ and the number is greater than a pre-determined minimum, indicates the presence of a biopsy needle in the US image.

According to some embodiments, needle detection module 390 is further configured to detect a needle distal tip, so as to locate accurately the location from where a biopsy sample is taken. According to some embodiments, the most distant stain 752 which is larger than $l_0$ is considered as the distal tip of the biopsy needle. In FIG. 3B stains 752a-752d are all larger than $l_0$, thus considered as valid image of respective portions of a biopsy needle. Stain 752e is smaller than $l_0$ thus not considered as an image of a portion of the biopsy needle. Consequently, a most distant point 752f on most distant stain 752d is registered as the position of biopsy needle distal tip.

As discussed above, continuous registration of location of biopsy gun 442 may be obtained using various methods in various embodiments of integrated system 300. Yet, in some embodiments, for registering a location in a patient's body from which a biopsy sample is taken, the time of the sampling event should be detected. Reference is made back to FIG. 2, schematically depicting a treatment tool interface module 350 of integrated system 300, functionally associated with main controller 330. Treatment tool interface module 350 is configured to receive and detect a signal from biopsy gun 442 indicating a biopsy sampling event. Treatment tool interface module 350 is further configured to register a time mark of detecting such a sampling event signal, thereby establishing substantially the time at which the sampling event had occurred, and to provide to main controller 330 such a detected and registered sampling event time. Main controller 330 is configured to detect and register the location of the sampling event by correlating the location of biopsy gun 442 and biopsy needle 444 as a function of time, with the sampling event time received from treatment tool interface module 350.

In some embodiments, biopsy gun 442 emits a distinctive sound during a sampling event. Treatment tool interface module 350 comprises a microphone 352 for receiving sound signals. Microphone 352 is positioned at a suitable distance from the treated patient and configured to receive sound signals in the work space around the patient. In some embodiments microphone 352 is positioned in a same room where the patient is treated for obtaining a biopsy sample thereof. In some embodiments microphone 352 is positioned proximal to a bed configured to support a treated patient. In some embodiments microphone 352 is positioned above a bed configured to support a treated patient. In some embodiments an optimal position of microphone 352 may be found during installation of integrated system 300 using a trial and error process. Microphone 352 is positioned sequentially in a series of positions and for each such positioning a reception test is carried out by activating biopsy gun 442 and measuring a respective received signal by microphone 352. An optimal position for microphone 352 is selected such that the received signal therein is the most desired (e.g. having the highest amplitude score in the reception test).

Figure 5:
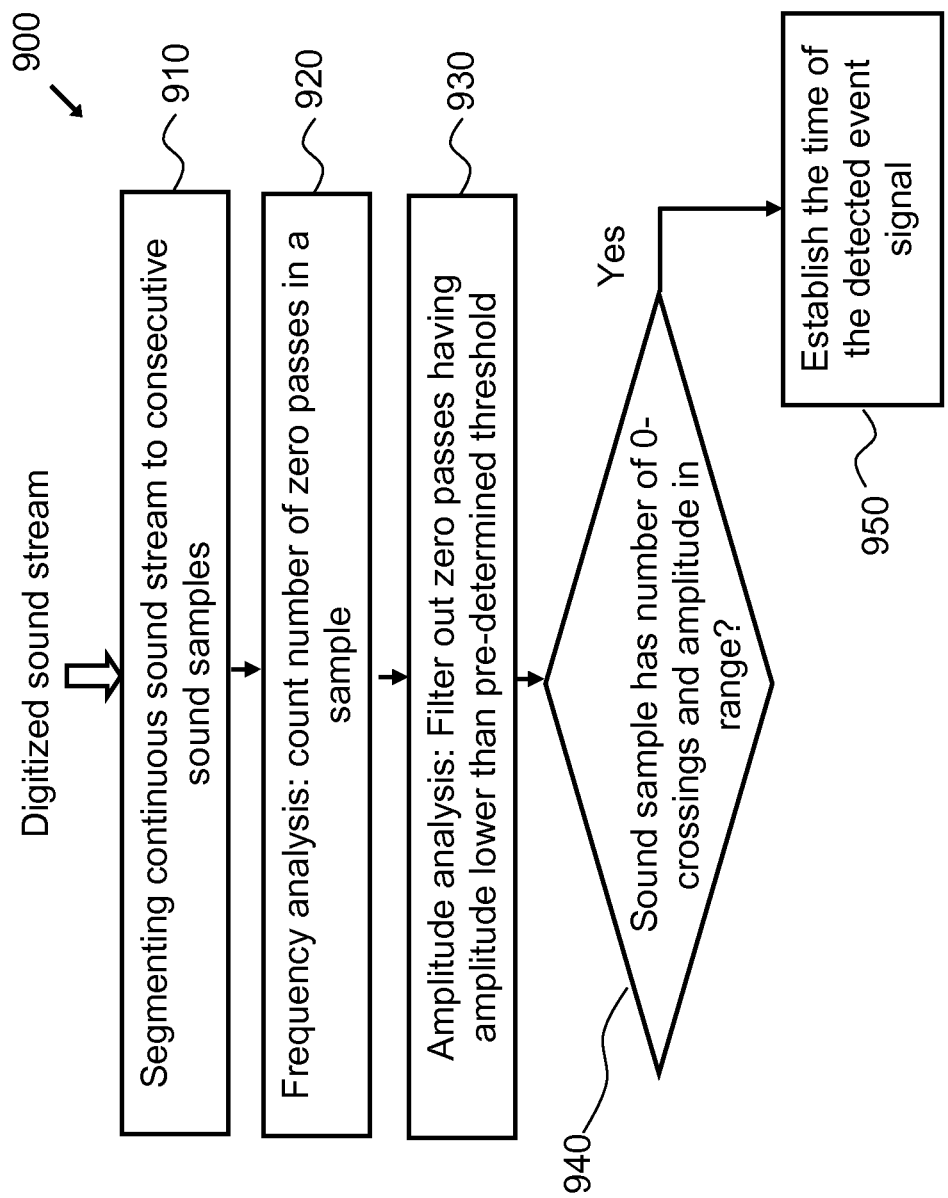

In some embodiments, biopsy gun 442 emits a distinctive sound. In some embodiments, the sound emitted by biopsy gun 442 is distinctive by having a dominant and specific spectral line. In some embodiments, the sound emitted by biopsy gun 442 is distinctive by having a specific acoustic spectrum. In some embodiments, the sound emitted by biopsy gun 442 is distinctive by having a specific combination of spectral signature and amplitude variation during the time of release of the biopsy needle. In some embodiments, the sound emitted by biopsy gun 442 is distinctive by having a dominant frequency component between 5 KHz and 7 KHz. Treatment tool interface module 350 further comprises a sound signal processor 354 configured to analyze received sound signals and detect a predefined sound signal, having specific amplitude and frequency characteristics, from the sound received by microphone 352. FIG. 5 illustrates schematically an embodiment of a method 900 for detecting a biopsy sampling event by treatment tool interface module 350. In step 910 the continuous sound signal received from microphone 352 is segmented to consecutive sound samples. For example, samples having a constant length in time of one-hundredth of a second may be so formed. In step 920, each sound sample is frequency-analyzed. According to some embodiments, such frequency analysis is accomplished by counting the number of times the analyzed sound signal crosses the zero base line in unit time. For example, a sound signal that crosses the zero base line 120 times in one-hundredth of a second is considered as a sound signal having a frequency of about 6 KHz. In step 930 an amplitude filtration is employed by sound signal processor 354 so as to filter out sound samples that are weaker (that is, having a smaller amplitude) than a pre-defined threshold A0. In step 940, sound samples having a number of zero crossings within a pre-defined range (e.g. between 100 zero-crossing per one-hundredth of a second and 140 zero-crossings per one-hundredth of a second) and having an amplitude greater than pre-defined value A0, are identified as indicating a biopsy sampling event. In step 950 the time of a sound sample detected as indicating a biopsy sampling event is established as the time of the biopsy sampling event and is provided by treatment tool interface module 350 to main controller 330. Main controller 330 correlates the time so received from treatment tool interface module 350 with location data of biopsy gun 442 and location data of biopsy needle 444 for establishing a locality of the biopsy sampling event.

According to some embodiments, a sampling time detected by treatment tool interface module 350 may be used to facilitate establishing a locus of a treatment event. According to some embodiments, method 800 for detecting a biopsy needle and a biopsy needle distal tip in an ultrasound image may comprise a step 810 prior to step 820 of method 800 of FIG. 4. According to some embodiments, a time $t_0$ identifying a sampling event and detected by treatment tool interface module 350 is provided to main controller 330 and used to select a small number of US images that were collected immediately before and immediately after $t_0$, for analysis by needle detection module 390. By analyzing only images that are collected within a time range coinciding with a biopsy sampling event, superfluous analysis effort is avoided, computer power is saved, and overall system resources of integrated system 300 are exploited more efficiently and more effectively. Moreover, risk of false detection of a biopsy needle in a US image by needle detection module is greatly reduced.

According to some embodiments, treatment tool interface module 350 is configured to detect a wirelessly transmitted radio signal indicating a treatment event. In some embodiments an event sensor 356 is attached to biopsy gun 442, configured to detect a sampling event and to transmit by radio waves a signal receivable by treatment tool interface module 350, indicating a sampling event. According to some embodiments event sensor 356 comprises an accelerometer, configured to detect recoil of biopsy gun 442 during a sampling event. According to some embodiments, event sensor 356 comprises a light sensitive sensor configured to receive light from biopsy needle 444 and configured to detect a rapid advancement of biopsy needle 444 by detecting rapid variations in light received thereto. According to some embodiments, event sensor 356 is connected by wires to event signal receiver 358.

Thus, according to an aspect of some embodiments there is provided an integrated system (100, 300) for facilitating local treatment in an organ. The integrated system comprises a tracking system (110, 310) functionally associated with at least one tracking sensor (112, 114, 116, 312, 314, 316). The tracking system is configured to provide position data comprising location and orientation of the tracking sensor along pre-selected coordinates (120, 320) substantially in real time. The integrated system further comprises a processing unit (130, 330), which is configured to receive image data from an imaging modality (200, 400) functionally associated with an imaging probe (202, 402). The imaging probe has a fixed spatial relationship with a tracking sensor (112, 312) which is functionally associated with the tracking system. The imaging probe is configured to collect image data of physical objects, wherein the image data corresponds to a region in space having a known spatial relationship with the location and orientation of the imaging probe at the time the image data is collected.

The processing unit (130, 330) is further configured to receive position data, corresponding to location and orientation of the tracking sensors (112, 114, 116, 312, 314, 316) from the tracking system (110, 310). The processing unit (130, 330) is further configured to assign image position data corresponding to position data associated with the tracking sensor attached to the imaging probe and received from the tracking system to image data received from the imaging modality.

The integrated system further comprises at least one from the group consisting of:
  an imaging system interface module (140, 340), functionally associated with the processing unit (130, 330) and configured to functionally associate with an imaging system (220, 420). The imaging system is capable of presenting to a user, through a user-interface device (222, 422), parameters indicating a mode of operation of the imaging system. The imaging system interface module is configured to receive at least one of the parameters from the user interface device or in parallel to the user interface device, and is further configured to interpret the at least one parameter and to allow the integrated system to assume a mode of operation according to the at least one parameter.
  a treatment tool interface module (150, 350), functionally associated with the processing unit (130, 330) and configured to functionally associate with a portable treatment tool (240, 440, 442, 444). The portable treatment tool has a known spatial relationship with a tracking sensor (114, 312) which is functionally associated with the tracking system (110, 310). The portable treatment tool is configured to provide a focused and local treatment to an organ. The treatment tool interface module is configured to receive and detect a treatment event signal from the portable treatment tool indicating a treatment event, thereby allowing the processing unit (130, 330) establish a time of the treatment event and thereby establish a locality of a treatment provided to the organ by the portable treatment tool.

According to some embodiments, the processing unit (330) comprises a 3D modeling module (370) configured to receive image data provided by an imaging modality and corresponding image position data. According to some embodiments, the 3D modelling module is further configured to create a virtual 3D model of an organ using suitably selected image data and image position data of the organ. According to some embodiments, the image data comprises a set of two-dimensional (2D) images of the organ. According to some embodiments, the integrated system further comprises the imaging modality.

According to some embodiments, the user interface device (222, 422) is a screen and the parameters are provided to the screen by video signals suitably adapted to display the parameters on the screen in a human comprehensible format. According to some embodiments, the imaging system interface module (140, 340) is configured to receive the video signals in parallel to the screen, to interpret the at least one parameter and to allow the integrated system assume a mode of operation according to the at least one parameter. According to some embodiments, the imaging system interface module (140, 340) is configured to receive the parameters from the screen by capturing a visual image of the parameters displayed on the screen, to interpret the at least one parameter and to allow the integrated system assume a mode of operation according to the at least one parameter.

According to some embodiments, the integrated system (300) further comprises a display (360), functionally associated with the processing unit (330), for displaying images corresponding to image data received from an imaging modality (400) by the processing unit (330). According to some embodiments, the imaging system (420) comprises the imaging modality (400) and is configured to display images corresponding to the image data collected by the imaging modality on a screen (422), in real time.

According to some embodiments, the imaging modality (400) is functionally associated with an ultrasound probe (402), comprising ultrasound transducers. According to some embodiments, the imaging modality is functionally associated with a magnetic excitation module. According to some embodiments, the imaging modality is functionally associated with an X-ray emitter. According to some embodiments, the integrated system (300) is further configured to assume a mode of operation upon receiving a parameter indicating a mode of operation of the imaging system (420) so that an image displayed on the display (360) of the integrated system is substantially the same as an image displayed on the screen (422) of the imaging system. According to some embodiments, the imaging system (420) comprises an ultrasonography system and the parameters are associated with at least one from the group consisting of: X scale, Y-scale, image freeze, split screen, flipped image and transverse/sagittal scan.

According to some embodiments, the signal from the portable treatment tool (240, 440, 442, 444) is received wirelessly by the treatment tool interface module (150, 350). According to some embodiments, the treatment tool interface module (350) comprises an event signal receiver (352, 358), configured to receive an event signal generated by the portable treatment tool. According to some embodiments, the event signal is a sound signal and the event signal receiver (352) is a microphone. According to some embodiments, the treatment tool interface module (350) comprises a signal processor (354) functionally associated with the event signal receiver (352, 358) and configured to analyze an event signal received by the event signal receiver and thereby to detect the treatment event signal.

According to some embodiments, the analysis is employed in the amplitude domain. According to some embodiments, the analysis is employed in the frequency domain. According to some embodiments, the analysis is employed in the frequency domain and in the amplitude domain. According to some embodiments, the analysis employs parameters pre-defined by a user. According to some embodiments, the analysis employs parameters established by the integrated system, by analyzing an exemplary treatment event signal. For example, main controller 330 may extract frequency and amplitude characterizing parameters from an exemplary sound sample recoding a sampling event, and employ such parameters to filter valid signals indicating a sampling event, from other sound and noise. According to some embodiments, the treatment tool (440, 442) comprises a biopsy needle (444). According to some embodiments, the treatment tool (440) comprises a biopsy gun (442) which emits a sound upon releasing the biopsy needle (444) to obtain a biopsy sample.

According to some embodiments, the integrated system (100, 300) is functionally associated with an imaging modality (200, 400) to receive image data substantially in real time from the imaging modality, and the imaging modality is functionally associated with an imaging probe (202, 402). The imaging probe has a known spatial relationship with a tracking sensor (112, 114, 312) of the tracking system (110, 310).

According to some embodiments, the processing (330) unit further comprises a needle detection module (390). The needle detection module is configured to detect an image of a needle in the received image data, and report needle position data obtained by the needle image detection. According to some embodiments, the needle detection module (390) is further configured to detect a needle distal tip, and subsequently report a location of the detected needle tip along the pre-defined set of coordinates (320).

According to some embodiments, the processing unit (330) further comprises a model registration module (380), functionally associated with the 3D modeling module (370). The model registration module (380) is configured to: receive a first virtual 3D model of an organ, with corresponding position data along a first pre-selected set of coordinates; receive a second virtual 3D model of the organ, with corresponding position data along a second pre-selected set of coordinates; and to transform at least one of the pre-selected set of coordinates of first virtual 3D model and the pre-selected set of coordinates of the second virtual 3D model, using shape-preserving transformations, so as to obtain a best fit between the first virtual 3D model and the second virtual 3D model. According to some embodiments, the first virtual 3D model and the second virtual 3D model are obtained from data received from a same imaging modality. According to some embodiments, the first virtual 3D model and the second virtual 3D model are obtained from data received from two different imaging modalities, respectively. According to some embodiments, one such imaging modality is functionally associated with an ultrasound probe, and the other imaging modality is functionally associated with a magnetic resonance excitation module.

According to an aspect of some embodiments, there is provided a method for facilitating local treatment in an organ. According to some embodiments, the method comprises providing an integrated system (100, 300) comprising: a tracking system (110, 310) functionally associated with at least one tracking sensor (112, 312) and configured to provide position data comprising location and orientation of the tracking sensor along pre-selected coordinates (120, 320) substantially in real time; a processing unit (130, 330), functionally associated with the tracking system (110, 310) to receive position data, corresponding to location and orientation of at least one tracking sensor (112, 312) from the tracking system (110, 310); and an imaging system interface module (140, 340), functionally associated with the processing unit (130, 330) and configured to functionally associate with an imaging system (220, 420) capable of presenting to a user, through a user-interface device (222, 422, parameters indicating a mode of operation of the imaging system.

The method further comprises providing an imaging system (220, 420) capable of presenting to a user, through a user-interface device (222, 422), parameters associated with a mode of operation of the imaging system. The method further comprises receiving, by the imaging system interface module (140, 340), at least one of the parameters from the user interface device (222, 422) or in parallel to the user interface device. The method further comprises assuming, by the integrated system (100, 300), a mode of operation according to the at least one parameter received from the imaging system (220, 420).

According to an aspect of some embodiments, there is provided a method for facilitating local treatment in an organ. According to some embodiments the method comprises providing an integrated system (100, 300) comprising: tracking system (110, 310) functionally associated with at least one tracking sensor (112, 312) and configured to provide data of location and orientation of the tracking sensor along pre-selected coordinates (120, 320) substantially in real time; a processing unit (130, 330), functionally associated with the tracking system (110, 310) to receive position data, corresponding to location and orientation of a tracking sensor from the tracking system; and a treatment tool interface module (150, 350), functionally associated with the processing unit (130, 330) and configured to functionally associate with a portable treatment tool (240, 440, 442, 444) having a known spatial relationship with a tracking sensor (114, 312) functionally associated with the tracking system (110, 310).

The method further comprises providing a portable treatment tool (240, 440, 442, 444) configured to provide a focused and local treatment to an organ and having a known spatial relationship with a tracking sensor (114, 312) functionally associated with the tracking system (110, 310). The method further comprises receiving by the treatment tool interface module (150, 350) a signal from the portable treatment tool (240, 440, 442, 444) indicating a treatment event. The method further comprises establishing a time of the treatment event using the signal from the portable treatment tool. The method further comprises establishing a locality of a treatment provided to the organ by the portable treatment tool.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. An integrated system for facilitating local treatment in an organ, comprising:
   a. a tracking system functionally associated with at least one tracking sensor and configured to provide position data comprising location and orientation of said tracking sensor along pre-selected coordinates substantially in real time, and
   b. a processing unit, configured to receive:
      image data from an imaging modality functionally associated with an imaging probe, said imaging probe having a fixed spatial relationship with a tracking sensor functionally associated with said tracking system wherein said imaging probe is configured to collect image data of physical objects, wherein the image data corresponds to a region in space having a known spatial relationship with the location and orientation of said imaging probe at the time the image data is collected, and
      position data, corresponding to location and orientation of said tracking sensor, from said tracking system,
      wherein said processing unit is further configured to assign image position data corresponding to position data of said tracking sensor received from said tracking system to image data received from said imaging modality,
   and said integrated system further comprises:
   c. an imaging system interface circuit, functionally associated with said processing unit and configured to functionally associate with an imaging system capable of presenting to a user, through a user-interface device, parameters indicating a mode of operation of said imaging system,
      wherein said imaging system interface circuit is configured to receive at least one of said parameters from said user interface device or in parallel to said user interface device, and is further configured to interpret said at least one parameter and to allow said integrated system to assume a mode of operation according to said at least one parameter, and
   d. a treatment tool interface circuit, comprising a microphone being other than said imaging probe and configured to receive a sound signal generated by said portable treatment tool, said treatment tool interface circuit being functionally associated with said processing unit and configured to functionally associate with a portable treatment tool having a known spatial relationship with a tracking sensor functionally associated with said tracking system and configured to provide a focused and local treatment to an organ,
      wherein said microphone of said treatment tool interface circuit is configured to receive and detect a treatment sound signal from said portable treatment tool indicating a treatment event, thereby allowing said processing unit establish a time of said treatment event and thereby establish a locality of a treatment provided to said organ by said portable treatment tool.

2. The integrated system of claim 1 wherein said processing unit comprises a 3D modelling circuit configured to receive image data provided by an imaging modality and corresponding image position data.

3. The integrated system of claim 2 wherein said 3D modelling circuit is further configured to create a virtual 3D model of an organ using suitably selected image data and image position data of said organ.

4. The integrated system of claim 3 wherein said image data comprises a set of two-dimensional (2D) images of said organ.

5. The integrated system of claim 3 wherein said processing unit comprises a model registration circuit, functionally associated with said 3D modeling circuit, and configured to:
receive a first virtual 3D model of an organ, with corresponding position data along a first pre-selected set of coordinates;
receive a second virtual 3D model of the organ, with corresponding position data along a second pre-selected set of coordinates;
transform at least one of the pre-selected set of coordinates of first virtual 3D model and the pre-selected set of coordinates of the second virtual 3D model, using shape-preserving transformations, so as to obtain a best fit between the first virtual 3D model and the second virtual 3D model.

6. The integrated system of claim 5 wherein the first virtual 3D model and the second virtual 3D model are obtained from data received from a same imaging modality.

7. The integrated system of claim 5 wherein the first virtual 3D model and the second virtual 3D model are obtained from data received from two different imaging modalities, respectively.

8. The integrated system of claim 7 wherein one imaging modality is functionally associated with an ultrasound probe, and the other imaging modality is functionally associated with a magnetic resonance excitation circuit.

9. The integrated system of claim 1 wherein said user interface device is a screen and said parameters are provided to said screen by video signals suitably adapted to display said parameters on said screen in a human comprehensible format.

10. The integrated system of claim 9 wherein said imaging system interface circuit is configured to receive said video signals in parallel to said screen, to interpret said at least one parameter and to allow said integrated system assume a mode of operation according to said at least one parameter.

11. The integrated system of claim 9 wherein said imaging system interface circuit is configured to receive said parameters from said screen by capturing a visual image of said parameters displayed on said screen, to interpret said at least one parameter and to allow said integrated system assume a mode of operation according to said at least one parameter.

12. The integrated system of claim 1 further comprising a display, functionally associated with said processing unit, for displaying images corresponding to image data received from an imaging modality by said processing unit.

13. The integrated system of claim 12 wherein said imaging system comprises said imaging modality and is configured to display images corresponding to said image data collected by said imaging modality on a screen, in real time.

14. The integrated system of claim 13 further configured to assume a mode of operation upon receiving said parameter so that an image displayed on said display of said integrated system is the same as an image displayed on said screen of said imaging system.

15. The integrated system of claim 13 wherein said imaging system comprises an ultrasonography system and said parameters are associated with at least one from the group consisting of: X scale, Y-scale, image freeze, split screen, flipped image and transverse/sagittal scan.

16. The integrated system of claim 1 wherein said imaging modality is functionally associated with an ultrasound probe, comprising ultrasound transducers.

17. The integrated system of claim 1 wherein said imaging modality is functionally associated with a magnetic excitation circuit.

18. The integrated system of claim 1 wherein said imaging modality is functionally associated with an X-ray emitter.

19. The integrated system of claim 1 wherein said signal from said portable treatment tool is received wirelessly by said treatment tool interface module.

20. The integrated system of claim 1 wherein said treatment tool interface circuit comprises a signal processor functionally associated with said microphone and configured to analyse an sound received by said microphone and thereby to detect said treatment event signal.

21. The integrated system of claim 20 wherein said analysis employs parameters established by said integrated system, by analysing an exemplary treatment sound signal.

22. The integrated system of claim 1 wherein said processing unit further comprises a needle detection circuit configured to:
detect an image of a needle in said received image data from said imaging modality, and
report needle position data obtained by said needle image detection.

23. The integrated system of claim 22 wherein said needle detection circuit is further configured to detect a needle distal tip, and subsequently report a location of the detected needle tip along said pre-defined set of coordinates.

24. The integrated system of claim 23 wherein said sound signal comprises sound of releasing said biopsy needle to obtain a biopsy sample.

25. The integrated system of claim 24 wherein a sound signal identified as a sound signal has a dominant frequency component between 5 KHz and 7 KHz.

26. The integrated system of claim 23 wherein a time of a treatment event established by said processing unit is employed to facilitate said detection of said biopsy needle or of said needle distal tip in said received image data.

* * * * *